United States Patent
Ichikawa et al.

(10) Patent No.: US 9,737,295 B2
(45) Date of Patent: Aug. 22, 2017

(54) SUTURE-NEEDLE HOLDER AND ENDOSCOPE SYSTEM

(71) Applicant: OLYMPUS CORPORATION, Hachioji-shi, Tokyo (JP)

(72) Inventors: Hiroaki Ichikawa, Yokohama (JP); Akihiro Shimazu, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/382,470

(22) Filed: Dec. 16, 2016

(65) Prior Publication Data
US 2017/0095249 A1    Apr. 6, 2017

Related U.S. Application Data

(63) Continuation of application No. PCT/JP2015/069276, filed on Jul. 3, 2015.

(30) Foreign Application Priority Data

Jul. 3, 2014 (JP) .................. 2014-137886

(51) Int. Cl.
*A61B 17/04* (2006.01)
*A61B 17/062* (2006.01)

(52) U.S. Cl.
CPC ...... *A61B 17/0469* (2013.01); *A61B 17/0625* (2013.01); *A61B 2017/047* (2013.01)

(58) Field of Classification Search
CPC ............ A61B 17/0469; A61B 17/0625; A61B 17/062; A61B 17/29; A61B 17/2909;
(Continued)

(56) References Cited

U.S. PATENT DOCUMENTS

| 5,458,608 A * | 10/1995 | Wortrich ......... A61B 17/00234 227/110 |
| 5,938,668 A | 8/1999 | Scirica et al. |
| 2010/0030237 A1 | 2/2010 | Hayashi et al. |

FOREIGN PATENT DOCUMENTS

| JP | 2005-161050 A | 6/2005 |
| JP | 2009-183690 A | 8/2009 |

(Continued)

OTHER PUBLICATIONS

Oct. 6, 2015 International Search Report issued in International Patent Application No. PCT/JP2015/069276.

*Primary Examiner* — Jonathan Miles
*Assistant Examiner* — Majid Jamialahmadi
(74) *Attorney, Agent, or Firm* — Oliff PLC

(57) ABSTRACT

A suture-needle holder includes: a sheath part; a grasping portion; an operation wire; and an operation part body formed to extend along a longitudinal axis, and connected such that the sheath part is movable in a direction aligned with the longitudinal axis and rotatable around the longitudinal axis. A first groove part having a distal end and a proximal end and extending along the longitudinal axis, and a second groove part having one end connected to the proximal end of the first groove part and the other end at a position separated from the one end in the direction aligned with the longitudinal axis and in a circumferential direction of the longitudinal axis, and extending from the one end to the other end are formed in the operation part body.

10 Claims, 8 Drawing Sheets

(58) Field of Classification Search
CPC ...... A61B 2017/047; A61B 2017/2936; A61B 2017/2929; A61B 2017/2933
USPC ........................................ 606/144, 205–207
See application file for complete search history.

(56) References Cited

FOREIGN PATENT DOCUMENTS

| | | |
|---|---|---|
| JP | 2010-036027 A | 2/2010 |
| WO | 2011/055684 A1 | 5/2011 |

* cited by examiner

SUTURE-NEEDLE HOLDER AND ENDOSCOPE SYSTEM

CROSS REFERENCE TO RELATED APPLICATIONS

This application is a continuation application based on a PCT Patent Application No. PCT/JP2015/069276, filed on Jul. 3, 2015, whose priority is claimed on Japanese Patent Application No. 2014-137886, filed Jul. 3, 2014, the entire content of which are hereby incorporated by reference.

BACKGROUND OF THE INVENTION

Field of the Invention

The present invention relates to a suture-needle holder for using a suture needle, and an endoscope system including this suture-needle holder.

Description of the Related Art

In the related art, as one of laparoscopic operation, or means for suturing an internal organ or the like via a treatment channel of a flexible endoscope, there is a suturing procedure, in which a suture needle to which suture thread is attached, and a suture-needle holder are combined together.

For example, a suture-needle holder described in Japanese Unexamined Patent Application, First Publication No. 2009-183690 is known as this type of suture-needle holder.

The suture-needle holder of Japanese Unexamined Patent Application, First Publication No. 2009-183690 is configured to include a coiled sheath (sheath part) having flexibility, a treatment part (grasping part) attached to a distal end of the coiled sheath, a wire (operation wire) connected to the treatment part, a main body connected to a proximal end of the coiled sheath, and an operation part connected to the main body.

The treatment part consists of first and second jaws (grasping members) for grasping a suture needle. A wire is connected to the second jaw.

A main body is formed of resin or the like and has hardness.

The operation part is constituted with a first handle (operation part body) attached to the main body, and a second handle (traction member) attached so as to be turnable in a certain range with respect to the first handle.

A distal end of the first handle is attached to a proximal end of the main body. A proximal end of the wire inserted through the main body extends toward a proximal end side of the first handle.

The second handle has a first end part turnably fixed to the first handle. The second handle is biased so as to be spaced apart from the first handle by an elastic force of a first biasing member attached to the first handle.

A link member to which the proximal end of the wire is connected to its first end part is attached to the second handle so as to be capable of turning between the first handle and the second handle. A second end part of the link member is turnably attached to the second handle.

In the suture-needle holder configured in this way, if both the handles are gripped and made to approach each other, the wire is pulled to a hand side, the second jaw of the treatment part turns to the distal end side, and the treatment part is closed. If both the handles are released, the first handle and the second handle are spaced apart from each other by a biasing force of the first biasing member. The wire moves forward to the main body side, a distal end of the second jaw turns to the proximal end side, and the treatment part is open.

SUMMARY

A suture-needle holder related to a first aspect of the present invention is a suture-needle holder. The suture-needle holder includes a sheath part capable of being inserted into the inside of the body; a grasping portion fixed to at a distal end part of the sheath part and capable of grasping a suture needle with an opening and closing operation; an operation wire connected to the grasping portion and operated to open and close the grasping portion by moving with respect to the sheath part along a longitudinal axis of the sheath part; and an operation part body formed to extend along the longitudinal axis, and connected to the sheath part such that the sheath part is movable in a direction aligned with the longitudinal axis and rotatable around the longitudinal axis. A first groove part having a distal end and a proximal end and extending along the longitudinal axis, and a second groove part having one end connected to the proximal end of the first groove part and the other end at a position separated from the one end in a direction aligned with the longitudinal axis and in a circumferential direction of the longitudinal axis, and extending from the one end to the other end are formed in the operation part body. The sheath part is provided with a protruding part that protrudes in a radial direction of the sheath part. The protruding part has a first state where the protruding part moves in a state where the protruding part is engaged with the first groove part, and a second state where the protruding part moves in a state where the protruding part is engaged with the second groove part. In the first state, the operation wire is pulled with respect to the operation part body, and thereby the protruding part is moved from a distal end side of the first groove part to a proximal end side of the first groove part and the grasping portion is closed to grasp the suture needle. In the second state, the operation wire in the first state is further pulled with respect to the operation part body, and thereby the protruding part is moved from the one end of the second groove part toward the other end of the second groove part, and the grasping portion and the sheath part are turned around the longitudinal axis with respect to the operation part body in a state where the grasping portion has grasped the suture needle.

According to the suture-needle holder related to a second aspect based on the above first aspect, the first groove part and the second groove part may be formed in the outer peripheral surface of the operation part body, and the protruding part may be provided at a proximal end part of the sheath part.

According to the suture-needle holder related to a third aspect based on the above second aspect, a third groove part having a distal end and a proximal end and extending along the longitudinal axis from the proximal end to the distal end, the proximal end being connected to the other end of the second groove part, and a fourth groove part extending around the longitudinal axis so as to connect the distal end of the third groove part and the distal end of the first groove part to each other may be formed in the outer peripheral surface of the operation part body. The protruding part has a third state where the protruding part moves in a state where the protruding part is engaged with the inside of the third groove part, and a fourth state where the protruding part moves in a state where the protruding part is engaged with the inside of the fourth groove part. In the third state, the protruding part is moved from the proximal end side toward the distal end side within the third groove part, and the grasping portion is opened to release the suture needle. In the fourth state, if the protruding part is moved from the one end toward the other end within the fourth groove part, the grasping portion and the sheath part are turned in a direction opposite to a direction of turning of the grasping portion and the sheath part in the second state in a state where the grasping portion is open.

According to the suture-needle holder related to a fourth aspect based on the above second aspect, an elastic member connected to the sheath part and the operation part body, respectively, may be further included.

According to the suture-needle holder related to a fifth aspect based on the above second aspect, a proximal end part of the operation wire may be provided with a traction member movably attached to the operation part body to move the operation wire in a direction aligned with the longitudinal axis with respect to the operation part body.

According to the suture-needle holder related to a sixth aspect based on the above fifth aspect, a ratchet mechanism may be further included that allows movement of the traction member to the proximal end side with respect to the operation part body and restricts movement of the traction member to the distal end side when the protruding part is disposed within the first groove part, and allows the movements of the traction member to the proximal end side and the distal end side with respect to the operation part body when the protruding part is disposed within the second groove part.

According to the suture-needle holder related to a seventh aspect based on the above second aspect, a recessed part that is recessed toward the distal end side, is capable of housing at least a portion of the protruding part and is formed at an end part on the first groove part side in a side surface of the second groove part on the distal end side.

According to the suture-needle holder related to an eighth aspect based on the above seventh aspect, a projecting part that protrudes toward the distal end side may be formed in a portion that faces the recessed part, in a side surface of the second groove part on the proximal end side.

According to the suture-needle holder related to a ninth aspect based on the above second aspect, a second projecting part may be formed at an end part on the second groove part side in a side surface of the first groove part.

According to an endoscope system related to a tenth aspect, the endoscope system may include the suture-needle holder based on the above second aspect; and an endoscope which has a flexible insertion part and a channel through which the suture-needle holder may be insertable into the insertion part.

DETAILED DESCRIPTION OF THE PREFERRED EMBODIMENTS

Hereinafter, one embodiment of an endoscope system related to the present invention will be described, referring to FIGS. 1 to 17.

Figure 1:
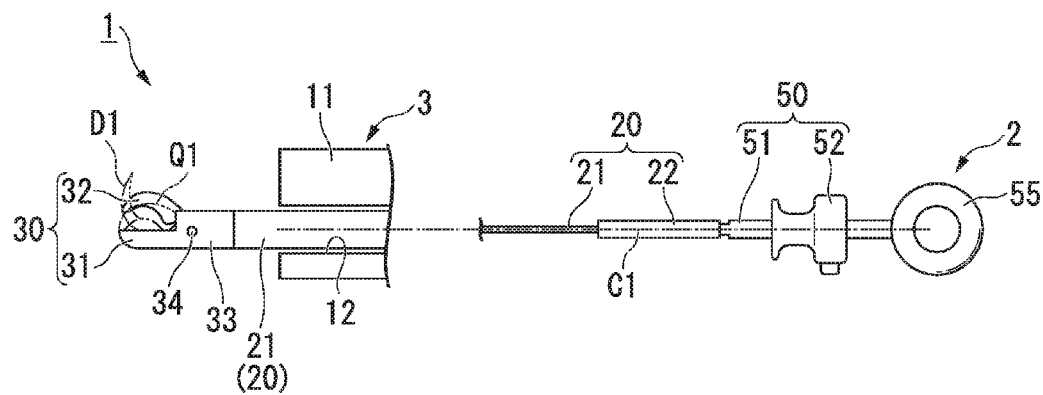
FIG. 1 is an overall cutaway view of a portion of an endoscope system of one embodiment of the present invention.

As illustrated in FIG. 1, the endoscope system 1 includes a suture-needle holder 2 of the present embodiment, and an endoscope 3. The endoscope 3 has an insertion part 11. A channel 12 through which the suture-needle holder 2 is instable is formed in the insertion part 11.

The configuration of the endoscope 3 is not particularly limited. For example, the endoscope 3 includes a flexible insertion part 11 to be inserted into the inside of a stomach from a mouth in the present embodiment.

Here, the term 'flexibility' means having bending rigidity (flexibility) to such a degree that the endoscope is deflected by operators, such as a surgeon.

The suture-needle holder 2 is used by being combined with a suture needle D1 that is, for example, a curved needle.

One end part of the suture thread D2 (refer to FIG. 8) is attached to the suture needle D1.

Figure 2:
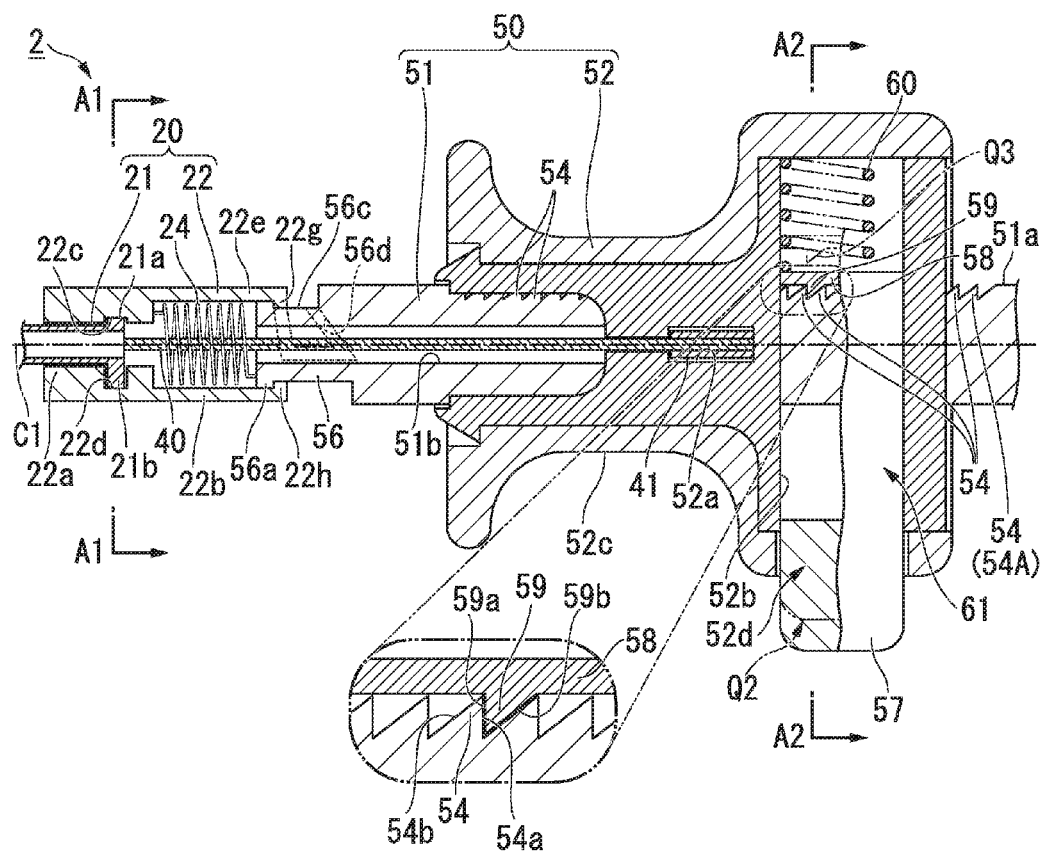
FIG. 2 is a sectional view of a side surface on a proximal end side in a suture-needle holder of the endoscope system.

As illustrated in FIGS. 1 and 2, the suture-needle holder 2 includes a sheath part 20 that is insertable into the inside of the body, a grasping part 30 that is provided at a distal end part of the sheath part 20, an operation wire 40 that is connected to the grasping part 30 and is movable relative to the sheath part 20 along a longitudinal axis C1 of the sheath part 20, and an operation part 50 that is connected to the to the sheath part 20.

In the following, the grasping part 30 side with respect to the operation part 50 is referred to as a distal end side, and the operation part 50 side with respect to the grasping part 30 is referred to a proximal end side.

Figure 3:
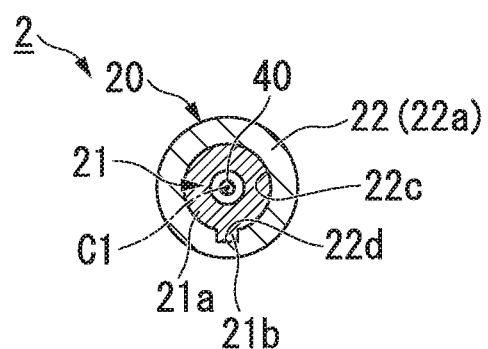
FIG. 3 is a sectional view taken along cutting line A1-A1 in FIG. 2.

As illustrated in FIGS. 2 and 3, the sheath part 20 has a flexible sheath 21, and a rotor 22 connected to a proximal end part of the sheath 21. A flange 21a is formed on an outer peripheral surface of the proximal end part of the sheath 21 over its entire circumference. A key protrusion 21b that protrudes from an outer peripheral surface of the flange 21a to a radial outer side of the sheath part 20 is formed in a portion of the sheath part 20 in a circumferential direction in an outer peripheral surface of the flange 21a.

The sheath 21 is formed of a material having flexibility, such as a coiled sheath. The flange 21a and the key protrusion 21b are integrally formed of metal, such as stainless steel or titanium, and are fixed to the proximal end part of the sheath 21 by welding or the like.

In the rotor 22, the internal diameter of at larger-diameter part 22b formed on the proximal end side of the rotor 22 is greater than the internal diameter of a smaller-diameter part 22a formed on the distal end side of the rotor 22 formed in a cylindrical shape.

An engaging groove 22c is formed on an inner peripheral surface of the smaller-diameter part 22a over its entire circumference.

A key groove 22d that extends from a bottom surface of the engaging groove 22c to the radial outer side is formed in a portion of the bottom surface of the engaging groove 22c in the circumferential direction.

Figure 4:
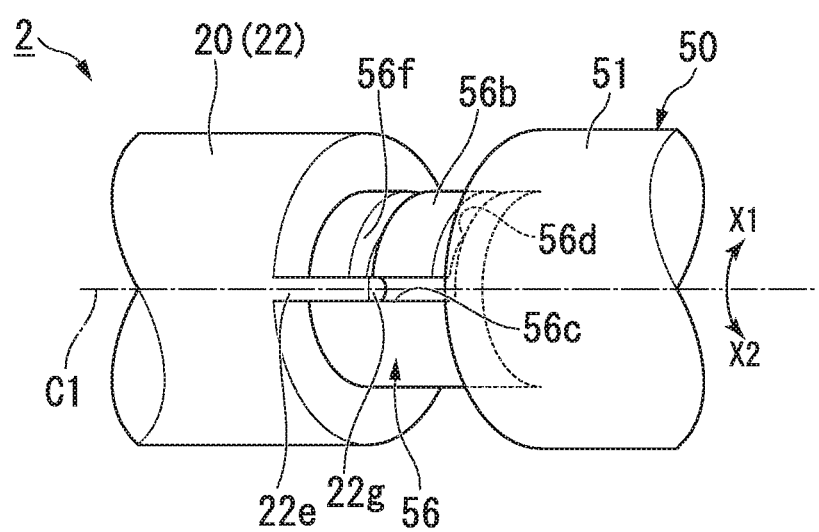
FIG. 4 is a perspective view of a sheath part and an operation part of the suture-needle holder.

As illustrated in FIGS. 2 and 4, a proximal end part of the larger-diameter part 22b is formed in the shape of a rod such that a cutout (its reference sign is omitted) is formed by both radial sides sandwiching a support part 22e being cut out, and thereby the support part 22e extends toward the proximal end side. A proximal end part of the support part 22e is provided with a protruding part 22g that protrudes to a radial inner side. The protruding part 22g is formed, for example, in a columnar shape.

An engaging part 22h is provided at the position of an inner peripheral surface of the proximal end part of the larger-diameter part 22b that faces the protruding part 22g. The engaging part 22h is formed, for example, in the shape of a rib that extends in the circumferential direction.

The smaller-diameter part 22a, the larger-diameter part 22b, the support part 22e, the protruding part 22g, and the engaging part 22h are integrally formed of metal, such as stainless steel or titanium.

The sheath 21 is inserted through the rotor 22, the flange 21a of the sheath 21 is engaged with the engaging groove 22c of the rotor 22, and the key protrusion 21b of the sheath 21 is engaged with the key groove 22d of the rotor 22. The engaging groove 22c, the flange 21a and the key groove 22d, and the key protrusion 21b are fixed with an adhesive, welding, or the like that is not illustrated.

By configuring the present invention in this way, the sheath 21 and the rotor 22 are integrated with each other, moved in a direction aligned with the longitudinal axis C1 or rotated around the longitudinal axis C1.

As illustrated in FIG. 2, the operation wire 40 is inserted through the sheath 21 and the rotor 22. A coil spring (elastic member) 24 is disposed within the larger-diameter part 22b of the rotor 22. A distal end part of the coil spring 24 is connected to a stepped part (its reference sign is omitted) that is formed between the smaller-diameter part 22a and the larger-diameter part 22b of the rotor 22.

The operation wire 40 is inserted into the coil spring 24.

As illustrated in FIG. 1, the grasping part 30 has a grasping member 31 and a grasping member 32. The grasping member 31 is fixed to the distal end part of the sheath 21 via a support member 33. The grasping member 32 is supported so as to be rotatable a pin 34 attached to the support member 33. A distal end part of the operation wire 40 is connected to a proximal end part of the grasping member 32 via a link member that is not illustrated.

FIG. 1 illustrates an open state where the operation wire 40 is moved to the distal end side to the sheath 21 and distal end parts of the grasping member 31 and the grasping member 32 are spaced apart from each other and are open. On the other hand, if the operation wire 40 is moved to the proximal end side with respect to the sheath 21, a closed state where the grasping member 32 moves to a position Q1 and the distal end parts of the grasping member 31 and the grasping member 32 approach each other and are closed is brought about. In this closed state, the suture needle D1 can be grasped between the grasping member 31 and the grasping member 32. That is, the operation wire 40 is connected to the grasping member 31 and the grasping member 32, and can be actuated by moving relative to the sheath 21 along the longitudinal axis of the sheath 21 such that the grasping member 31 and the grasping member 32 are open and closed therebetween.

The operation wire 40 is formed of a single wire, a stranded wire, or the like. A tubular fixing member 41 illustrated in FIG. 2 is attached to a proximal end part of the operation wire 40 by brazing or the like.

Figure 5:
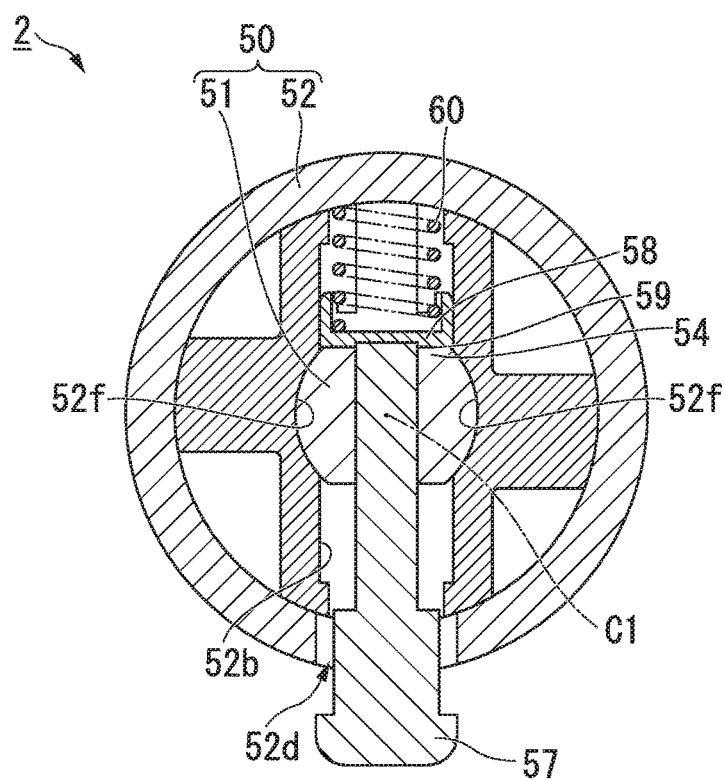
FIG. 5 is a sectional view taken along cutting line A2-A2 in FIG. 2.

As illustrated in FIGS. 2 and 5, the operation part 50 is formed in a shaft shape extending along the longitudinal axis C1, and has an operation part body 51 that is connected to the rotor 22 of the sheath part 20, and a slider (traction member) 52 that is slidably provided along the longitudinal axis C1 with respect to the operation part body 51. In this example, the operation part 50 is a so-called slider-type handle.

The operation part body 51 is grasped by a surgeon. A plurality of tooth parts 54 are formed along the longitudinal axis C1 in a side surface 51a parallel to the longitudinal axis C1 of the operation part body 51. As illustrated in the enlarged view in FIG. 2, an orthogonal surface 54a orthogonal to the longitudinal axis C1 and an inclined surface 54b spaced apart from the longitudinal axis C1 as it becomes closer to the proximal end side is formed in each tooth part 54.

A finger hooking ring 55 is attached to a proximal end part of the operation part body 51 (refer to FIG. 1).

As illustrated in FIGS. 2 and 4, the smaller-diameter part 56 having a smaller external diameter than the proximal end side is formed at a distal end part of the operation part body 51. The section of the smaller-diameter part 56 by a plane orthogonal the longitudinal axis C1 is formed in a cylindrical shape.

A flange 56a is formed on an outer peripheral surface of a distal end part of the smaller-diameter part 56 over its entire circumference. The smaller-diameter part 56 of the operation part body 51 is inserted into the larger-diameter part 22b of the rotor 22. The flange 56a of the operation part body 51 and the engaging part 22h of the rotor 22 are engaged with each other, and the smaller-diameter part 56 of the operation part body 51 and rotor 22 slide on each other. Accordingly, the operation part body 51 of the operation part 50 can move in a direction aligned with the longitudinal axis C1 and around the longitudinal axis C1 with respect to the sheath part 20.

Figure 6:
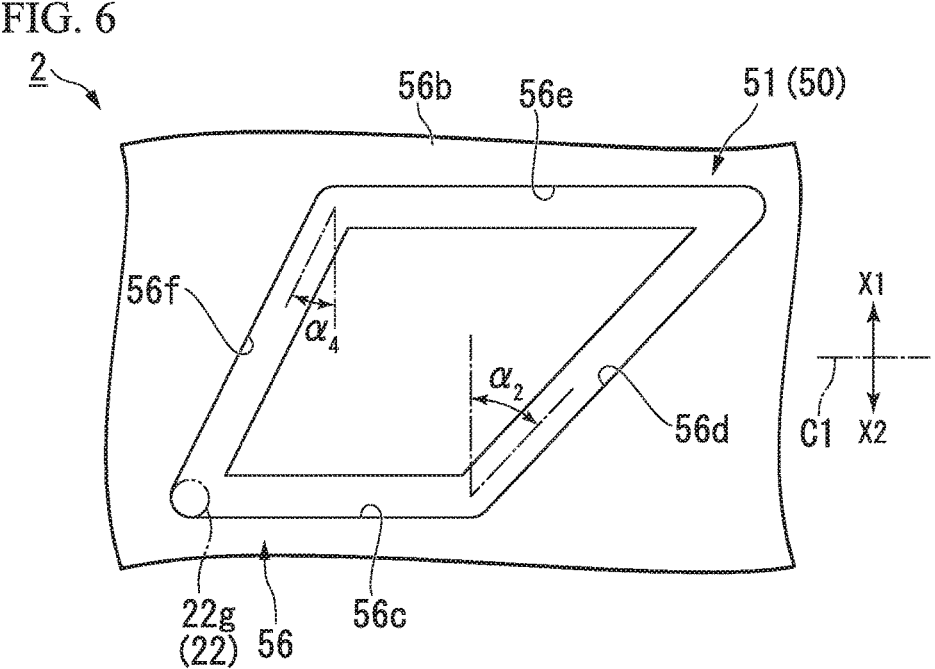
FIG. 6 is a deployed view of an outer peripheral surface of the operation part of the suture-needle holder.

As illustrated in FIGS. 4 and 6, a first groove part 56c and a second groove part 56d are formed in an outer peripheral surface 56b of the smaller-diameter part 56. The first groove part 56c has a distal end and a proximal end, and extends along the longitudinal axis C1 from the distal end to the proximal end. The second groove part 56d has one end connected to the proximal end of the first groove part 56c, and the other end at a position spaced apart from the one end in a spiral direction around the longitudinal axis C1, extends from one end to the other end, and is spirally formed. Moreover, a third groove part 56e and a third fourth groove part 56f are formed in the outer peripheral surface 56b of the smaller-diameter part 56. The third groove part 56e has a distal end and a proximal end, the proximal end is connected to the other end of the second groove part, and extends along the longitudinal axis C1 from the proximal end to the distal end. The fourth groove part 56f extends around the longitudinal axis C1 so as to connect the distal end of the third groove part and the distal end of the first groove part to each other, and the fourth groove part 56f that is spirally formed is exemplified in the present embodiment.

The groove parts 56c and 56e are linearly formed. The length of the first groove part 56c in the longitudinal axis C1 is equal to or smaller than the total length (the pitch of the tooth parts 54×the number of the tooth parts 54) of the plurality of tooth parts 54 in the longitudinal axis C1.

The second groove part 56d extends toward a first side (first direction) X1 around the longitudinal axis C1 as it becomes closer to the proximal end side. The fourth groove part 56f extends toward a second side (second direction) X2 around the longitudinal axis C1 as it becomes closer to the distal end side. A distal end of the fourth groove part 56f is connected to the distal end of the first groove part 56c. The groove parts 56d and 56f are formed in a spiral shape having the longitudinal axis C1 as a spiral axis. A lead angle α4 of the fourth groove part 56f is smaller than a lead angle α2 of the second groove part 56d.

The width of the groove parts 56c, 56d, 56e, and 56f is slightly greater than the external diameter of the protruding part 22g of the rotor 22.

The protruding part 22g of the rotor 22 are engaged with the groove parts 56c, 56d, 56e, and 56f, and are movable (slidable) along the groove parts 56c, 56d, 56e, and 56f.

In a first state where the protruding part 22g is engaged with the inside of first groove part 56c and moves, the protruding part 22g moves from the distal end side to the proximal end side within the first groove part 56c by pulling the operation wire 40 with respect to the sheath 21 (operation part body), the grasping members 31 and 32 become from the open state into the closed state, and grasp the suture needle D1.

In a second state where the protruding part 22g is engaged with the inside of the second groove part 56d and moves, the operation wire 40 in the first state is further pulled, and thereby the protruding part 22g moves from one end toward the other end within the second groove part 56d, and the rotor 22, the sheath 21, and the grasping part 30 are integrated with each other together with the protruding part 22g, and rotates around the longitudinal axis C1 along the second groove part 56d. That is, in a state the suture needle D1 is grasped by the grasping members 31 and 32, the grasping part 30 is turned around the longitudinal axis C1 with respect to the operation part body 51 together with the sheath 21, and the suture needle D1 is punctured into tissue.

In a third state where the protruding part 22g is engaged with the inside of the third groove part 56e and moves, the protruding part 22g moves from the proximal end side toward the distal end side within the third groove part 56e, the operation wire 40 moves to the distal end side with respect to the sheath 21, and the grasping members 31 and 32 are brought into the open state from the closed state, and releases the suture needle D1.

In a fourth state where the protruding part 22g is engaged with the inside of the fourth groove part 56f and moves, the protruding part 22g moves from one end toward the other end within the fourth groove part 56f, and the rotor 22, the sheath 21, and the grasping part 30 are integrated with each other together with the protruding part 22g, and rotates around the longitudinal axis C1 along the fourth groove part 56f. That is, in a state where the grasping members 31 and 32 are spaced apart from each other and are open, the grasping part 30 rotates in a direction opposite to the direction of the rotation in the second state together with the sheath 21.

As illustrated in FIG. 2, a proximal end part of the coil spring 24 is connected to a distal end surface of the smaller-diameter part 56 of the operation part body 51.

A slit 51b is formed on the longitudinal axis C1 of the operation part body 51. The operation wire 40 is inserted through the slit 51b.

A recess 52a is formed on the longitudinal axis C1 in the slider 52. The fixing member 41 is disposed within the recess 52a, and the slider 52 is fixed to the proximal end part of the operation wire 40 by the fixing member 41 being engaged with the recess 52a.

A slit 52f that extends along the longitudinal axis C1 illustrated in FIG. 5 is formed in the slider 52. The slider 52 can slide along the longitudinal axis C1 with respect to the operation part body 51 by the operation part body 51 being inserted through the slit 52f.

As illustrated in FIG. 2, a recess 52b that extends in a direction intersecting the longitudinal axis C1 from an outer surface of the slider 52 is formed on the proximal end side of the slider 52. A finger-hooking recess 52c is formed in an outer surface of the slider 52 around the longitudinal axis C1.

A button 57 is inserted through an opening 52d that communicates with the outside in the recess 52b.

A coupling plate 58 is provided opposite to the opening 52d across the longitudinal axis C1 within the recess 52b of the slider 52. The coupling plate 58 is connected to the button 57. A tooth part 59 is formed on the surface of the coupling plate 58 on the side of the longitudinal axis C1. As illustrated in the enlarged view in FIG. 2, an orthogonal surface 59a orthogonal to the longitudinal axis C1 and an inclined surface 59b spaced apart from the longitudinal axis C1 as it becomes closer to the proximal end side are formed in the tooth part 59.

A coil spring 60 is disposed between a bottom surface of the recess 52b of the slider 52, and the coupling plate 58. The coil spring 60 biases the coupling plate 58 to the longitudinal axis C1 side.

In addition, a ratchet mechanism 61 is constituted by the plurality of tooth parts 54, the button 57, the coupling plate 58, the tooth part 59, and the coil spring 60.

When the orthogonal surface 59a of the tooth part 59 of the coupling plate 58 comes into contact with the orthogonal surfaces 54a of the plurality of tooth parts 54 of the operation part body 51, the tooth part 59 is inhibited from moving to the distal end side with respect to the tooth parts 54. In this case, the slider 52 is inhibited from moving to the distal end side with respect to the operation part body 51 by the coupling plate 58 in which the tooth part 59 is formed being locked to an inner peripheral surface of the recess 52b.

The inclined surface 59b of the tooth part 59 slides on the inclined surfaces 54b of the plurality of tooth parts 54, so that the slider 52 can be moved to the proximal end side with respect to the operation part body 51 even if the tooth part 59 of the coupling plate 58 comes into contact with the tooth parts 54 of the operation part body 51.

Meanwhile, the button 57 is moved and pushed in up to a position Q2 to the longitudinal axis C1 side while elastically deforming the coil spring 60. In this case, movement of the tooth parts 54 up to a position Q3, prevents the tooth part 59 of the coupling plate 58 from coming into contact with the tooth parts 54 of the operation part body 51. As a result, the slider 52 can be moved to both the distal end side and the proximal end side with respect to the operation part body 51.

When the protruding part 22g is disposed at the proximal end part within the first groove part 56c, a tooth part 54A located closest to the proximal end side among the plurality of tooth parts 54 and the tooth part 59 are engaged with each other. That is, when the protruding part 22g is disposed within the first groove part 56c, the tooth parts 54 and the tooth part 59 are engaged with each other, but when the protruding part 22g is disposed within the second groove part 56d, the tooth parts 54 and the tooth part 59 are not engaged with each other.

In this way, when the protruding part 22g is disposed within the first groove part 56c in a state where a button 57 is not pushed in, the slider 52 is inhibited from moving to the distal end side with respect to the operation part body 51, and is allowed to move to the proximal end side. When the protruding part 22g is disposed within the second groove part 56d, the slider 52 is also allowed to move to any of the distal end side and the proximal end side with respect to the operation part body 51.

If the slider 52 is operated and the slider 52 is moved (pulled back) to the proximal end side with respect to the operation part body 51, the operation wire 40 moves to the proximal end side with respect to the operation part body 51, and the sheath 21, and the grasping members 31 and 32 is brought into the closed state.

On the other hand, if the slider 52 is moved (pushed in) to the distal end side with respect to the operation part body 51, the operation wire 40 moves to the distal end side with respect to the operation part body 51 and the sheath 21 and the grasping members 31 and 32 is brought into the open state.

Next, the operation of the endoscope system 1 constituted as described above will be described. In the following, a description will be made taking a procedure in which the tissue that is a treatment target part formed inside a patient's stomach is sutured as an example.

The protruding part 22g is disposed within a proximal end part of the third groove part 56e outside a patient's body, and the grasping members 31 and 32 are brought into the closed state. The insertion part 11 of the endoscope 3 is inserted from a natural opening, such as a patient's mouth, and the insertion part 11 is held in a state where a distal end surface thereof is made to face the tissue that is a treatment target part.

The sheath part 20 of the suture-needle holder 2 is inserted from the proximal end part of the channel 12 of the endoscope 3, and the grasping part 30 is made to protrude from a distal end part of the channel 12.

A surgeon grasps the operation part 50 by passing the thumb of his/her one hand through the finger hooking ring 55 of the operation part body 51 and hanging his/her index finger and middle finger on the finger-hooking recess 52c of the slider 52.

If the slider 52 is pushed in and the protruding part 22g is disposed at a distal end part of the fourth groove part 56f, that is, a distal end part of the first groove part 56c, the grasping members 31 and 32 are brought into the open state, and are turned to the second side (second direction) X2 around the longitudinal axis C1.

Figure 7:
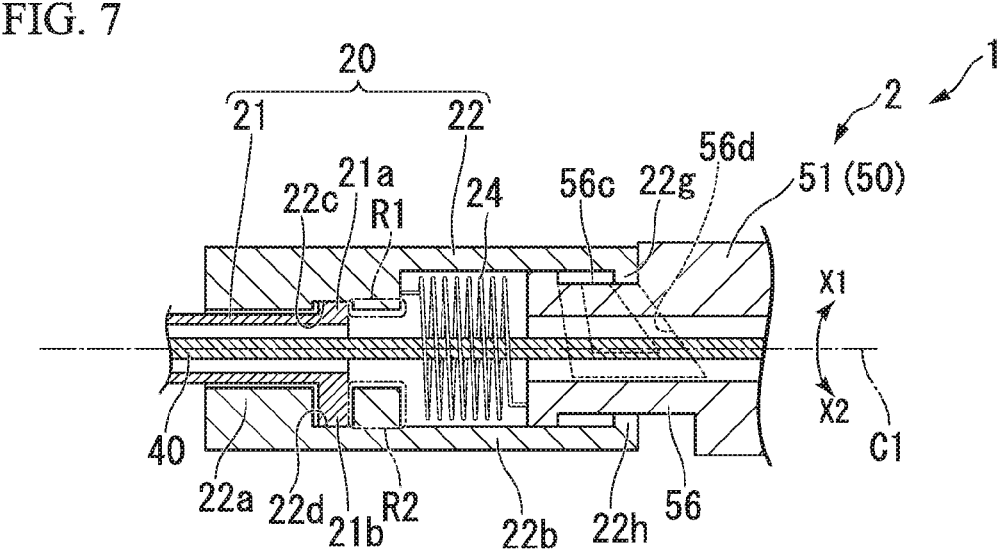
FIG. 7 is a sectional view of main parts illustrating the operation of the endoscope system of the embodiment of the present invention.
Figure 8:
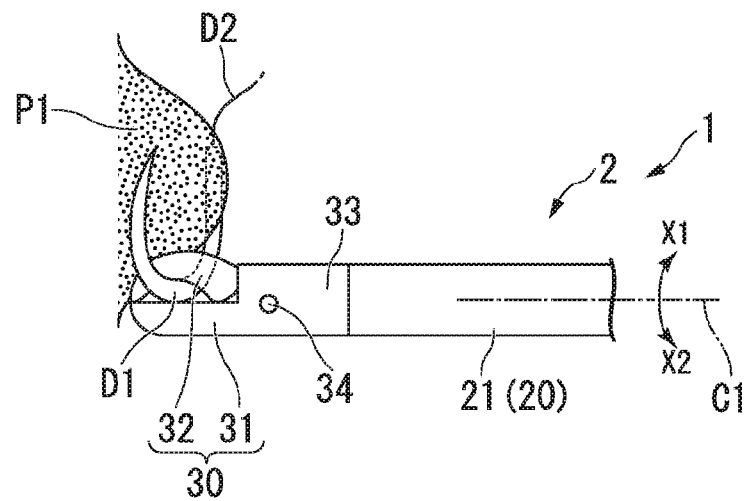
FIG. 8 is a side view illustrating the operation of the endoscope system.

The suture needle D1 conveyed inside the stomach by conveying means that is not illustrated is disposed between the grasping member 31 and the grasping member 32. The slider 52 is pulled back from a state where the protruding part 22g is disposed at the distal end part of the first groove part 56c. Accordingly, as illustrated in FIGS. 7 and 8, the protruding part 22g moves to the proximal end side inside the first groove part 56c, the operation wire 40 moves to the proximal end side with respect to the sheath part 20, and the grasping members 31 and 32 are brought into the closed state and grasp the suture needle D1.

In this case, the coil spring 24 is compressed in the direction aligned with the longitudinal axis C1 more than a state where the coil spring has a natural length. Since the plurality of tooth parts 54 and the tooth part 59 of the ratchet mechanism 61 are engaged with each other, the slider 52 can be pulled back, but the pulled-back slider 52 cannot be pushed in at a time.

The surgeon pushes in the suture-needle holder 2 or adjusts the orientation in which a bending part (not illustrated) of the insertion part 11 of the endoscope 3 bends, thereby adjusting a positional relationship between tissue P1 and the suture needle D1.

Figure 9:
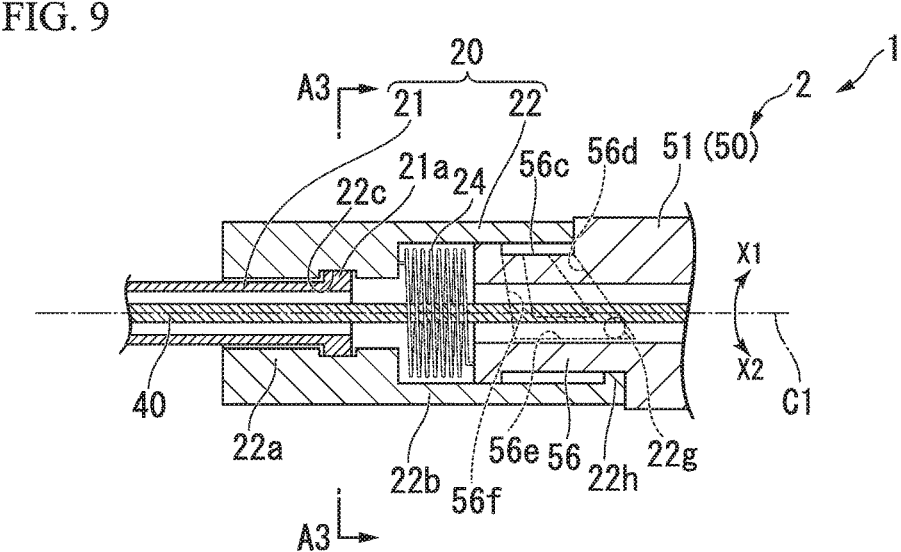
FIG. 9 is a sectional view of the main parts illustrating the operation of the endoscope system.
Figure 10:
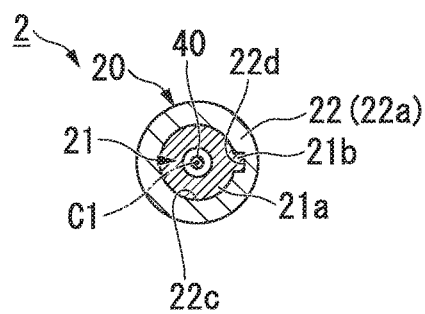
FIG. 10 is a sectional view taken along cutting line A3-A3 in FIG. 9.
Figure 11:
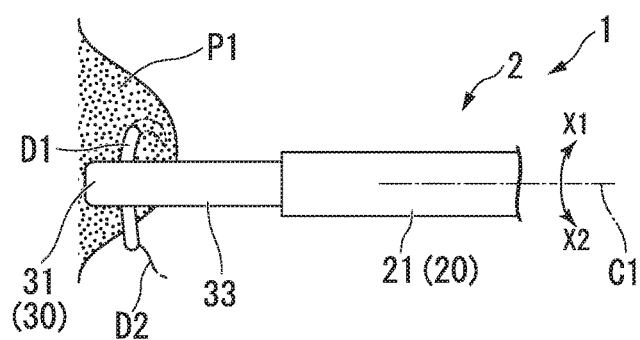
FIG. 11 is a side view illustrating the operation of the endoscope system.

If the slider 52 is further pulled back, as illustrated in FIGS. 9 to 11, the protruding part 22g moves to the proximal end side inside the second groove part 56d, and the grasping members 31 and 32 and the sheath part 20 turn to the first side (first direction) X1 around the longitudinal axis C1 with respect to the operation part body 51. In this case, the coil spring 24 is further compressed in the direction aligned with the longitudinal axis C1, and the tissue P1 is punctured with a distal end part of the suture needle D1.

The proximal end side of the coil spring 24 is twisted to the first side (first direction) X1 around the longitudinal axis C1.

In this way, simply by the surgeon pulling back the slider 52, an operation in which the grasping members 31 and 32 are brought into the closed state and grasp the suture needle D1 and an operation in which the tissue P1 is punctured with the suture needle D1 are continuously performed. Since the grasping members 31 and 32 are in the closed state when the protruding part 22g is disposed within the second groove part 56d, the tissue P1 can be punctured with the suture needle D1 in a state where the suture needle D1 is reliably grasped.

When these operations including the grasping of the suture needle D1 and the puncturing of the tissue P1 have ended, the protruding part 22g is disposed at a proximal end part of the second groove part 56d.

In addition, when the protruding part 22g is disposed within the second groove part 56d, the plurality of tooth parts 54 and tooth parts 59 of the ratchet mechanism 61 are not engaged with each other. Therefore, the suture needle D1 can be extracted from the tissue P1 by pushing in the slider 52 to turn the grasping part 30 to the second side (second direction) X2 around the longitudinal axis C1. In this case, the protruding part 22g cannot be moved up to the inside of the first groove part 56c by the ratchet mechanism 61.

A place where the tissue P1 is punctured with the suture needle D1 is adjusted, and the slider 52 is pulled back, and the tissue P1 is punctured with the suture needle D1.

Figure 12:
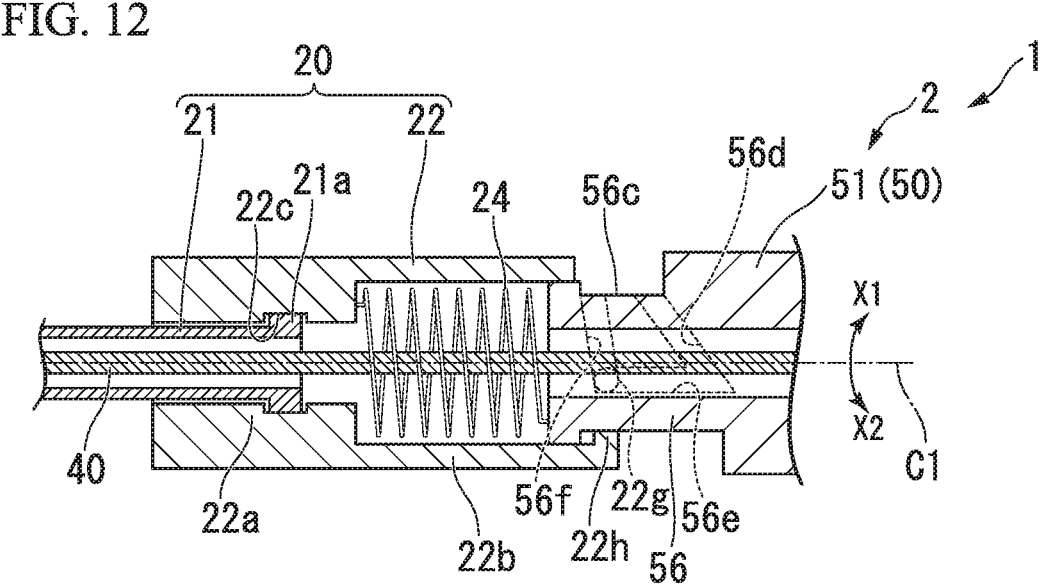
FIG. 12 is a sectional view of the main parts illustrating the operation of the endoscope system.

If a force with which the surgeon pulls back the slider 52 from a state where the protruding part 22g is disposed at the proximal end part of the second groove part 56d is loosened, the protruding part 22g, as illustrated in FIG. 12, is moved to the distal end side inside the third groove part 56e with the elastic force of the coil spring 24, and the grasping members 31 and 32 are brought into the open state and releases the suture needle D1. Since the lead angle α4 of the fourth groove part 56f is smaller than the lead angle α2 of the second groove part 56d, the positions of the grasping members 31 and 32 when releasing the suture needle D1 become closer to the distal end side.

If the force with which the slider 52 is pulled back is further loosened, the protruding part 22g is moved to the distal end side inside the fourth groove part 56f by the elastic force of the coil spring 24. In this case, the grasping members 31 and 32 and the sheath part 20 turn to the second side (second direction) X2 around the longitudinal axis C1 with respect to the operation part body 51. That is, the orientations of the grasping members 31 and 32 around the longitudinal axis C1 return to the orientations when the grasping members 31 and 32 grasp the suture needle D1.

Figure 13:
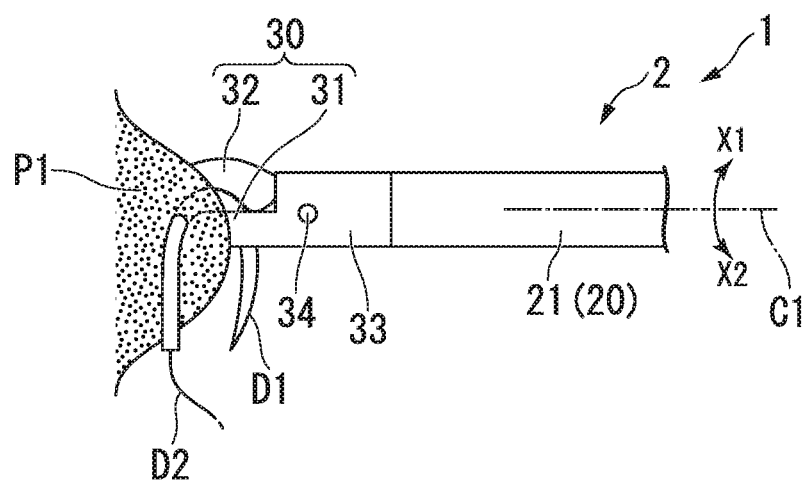
FIG. 13 is a side view illustrating the operation of the endoscope system.

Thereafter, the slider 52 is pulled back if necessary, and as illustrated in FIG. 13, the grasping members 31 and 32 are brought into the closed state, and the distal end part of the suture needle D1 is re-grasped, that is, re-held.

If the slider 52 is further pulled back, the grasping member 31 and 32 and the like turn to the first side (first direction) X1 around the longitudinal axis C1, the suture needle D1 passes through the tissue P1, and suture thread D2 passes through the tissue P1.

In this way, simply by the surgeon pushing in the slider 52, an operation in which the grasping members 31 and 32 are brought into the open state and releases the suture needle D1 and an operation in which the orientation of the grasping part 30 returns are continuously performed. The operation of pulling back or pushing in the slider 52 is repeated, and the tissue P1 is sutured.

As described above, according to the suture-needle holder 2 and the endoscope system 1 of the embodiment, if the slider 52 is pulled back, the operation in which the grasping members 31 and 32 are brought into the closed state and grasp the suture needle D1 and an operation in which the sheath part 20 is turned to the first side (first direction) X1 around the longitudinal axis C1 and the tissue P1 is punctured with the suture needle D1 are continuously performed. Consequently, simply by pulling back the slider 52, the rotation operation of the sheath part 20 can also be performed and the operability of the slider 52 and the sheath part 20 can be improved.

Even if the force that pulls back the slider 52 when the protruding part 22g is disposed within the second groove part 56d (while the grasping part 30 is rotated around the longitudinal axis C1) is loosened and is open, the protruding part 22g do not move into the first groove part 56c. Consequently, the suture needle D1 is not open unintentionally.

The groove parts 56e and 56f are formed in the outer peripheral surface 56b of the operation part body 51. If the slider 52 is pushed in, an operation in which the suture needle D1 is released, and an operation in which the sheath part 20 is turned to the second side (second direction) X2 around the longitudinal axis C1 are continuously performed. Consequently, simply by pushing in the slider 52, the rotation operation of the sheath part 20 can also be performed and the operability of the slider 52 and the sheath part 20 can be further improved.

The suture-needle holder 2 includes the coil spring 24, so that the slider 52 can be moved to the distal end side by the elastic force of the coil spring 24 even if the slider 52 is not pushed in after the slider 52 is pulled back.

The suture-needle holder 2 including the ratchet mechanism 61, so that the suture needle D1 once grasped by the grasping members 31 and 32 can be prevented from being released, and the puncturing position of the tissue P1 by the suture needle D1 can be easily adjusted.

When the tooth part 59 is not locked to the plurality of tooth parts 54, the protruding part 22g moves from the first groove part 56c to the second groove part 56d. Consequently, by the locking between the plurality of tooth parts 54 and the tooth part 59, the open/closed state of the grasping members 31 and 32 can be detected and the opening/closing operation of the grasping members 31 and 32 can be easily performed.

The configuration of the suture-needle holder 2 of the present embodiment can be variously deformed as described below.

Figure 14:
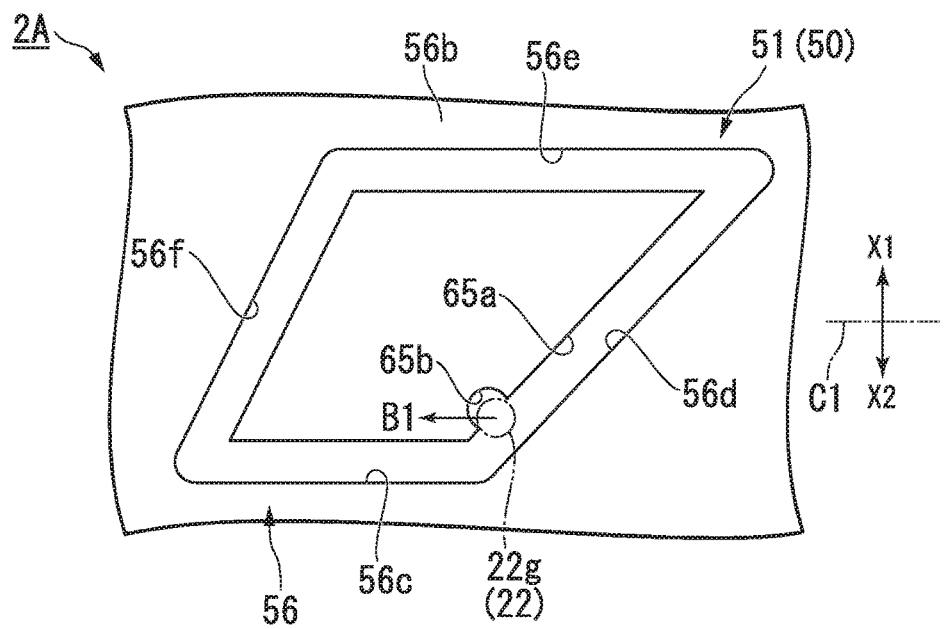
FIG. 14 is a deployed view of an outer peripheral surface of an operation part of a suture-needle holder in a modification example of the embodiment of the present invention.

For example, as in a suture-needle holder 2A illustrated in FIG. 14, a recessed part 65b may be formed at an end part on the first groove part 56c side in a side surface 65a on the distal end side of the second groove part 56d. The recessed part 65b is recessed toward the distal end side so as to house at least a portion of the protruding part 22g.

An elastic force to move the protruding part 22g to the distal end side like an arrow B1 is exerted on the protruding part 22g by the coil spring 24.

If the protruding part 22g is housed within the recessed part 65b, the protruding part 22g does not easily comes out of the recessed part 65b even if the elastic force is exerted on the protruding part 22g like the arrow B1. Consequently, the protruding part 22g can be more reliably prevented from returning to the inside of the first groove part 56c from the inside of the second groove part 56d.

Figure 15:
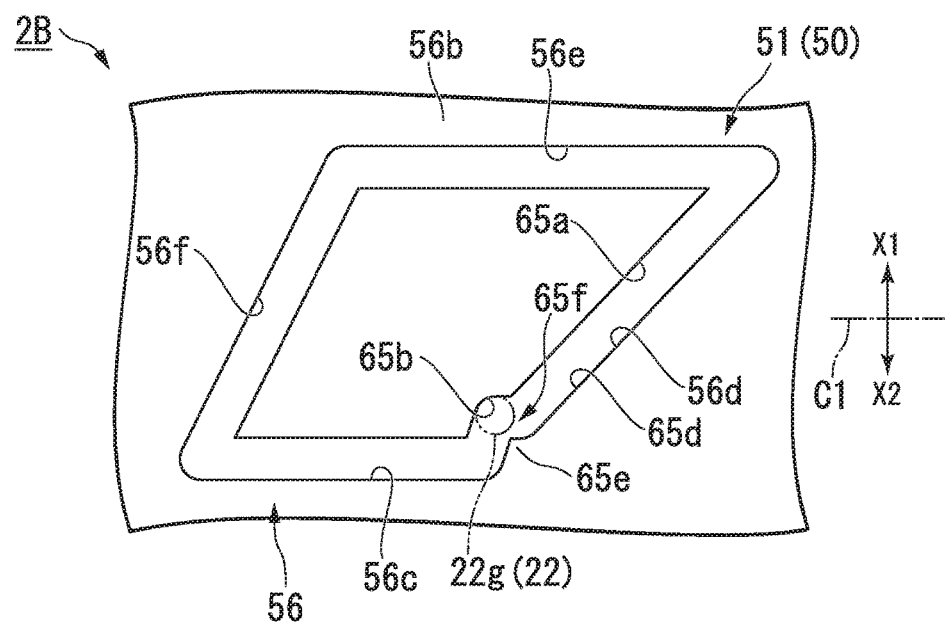
FIG. 15 is a deployed view of an outer peripheral surface of an operation part of a suture-needle holder in a modification example of the embodiment of the present invention.

In addition, as in a suture-needle holder 2B illustrated in FIG. 15 a projecting part 65e may be formed in a side surface 65d of the second groove part 56d on the proximal end side, in addition to the respective components of the suture-needle holder 2A of the above modification example. The projecting part 65e is formed in the portion of the side surface 65d facing the recessed part 65b so as to protrude toward the distal end side. A meandering part 65f in which the second groove part 56d meanders is formed by the projecting part 65e and the recessed part 65b. The width of the meandering part 65f is set such that the protruding part 22g passes therethrough.

The protruding part 22g that has entered the recessed part 65b once does not easily come out of the recessed part 65b by forming the projecting part 65e and the recessed part 65b in the second groove part 56d.

Figure 16:
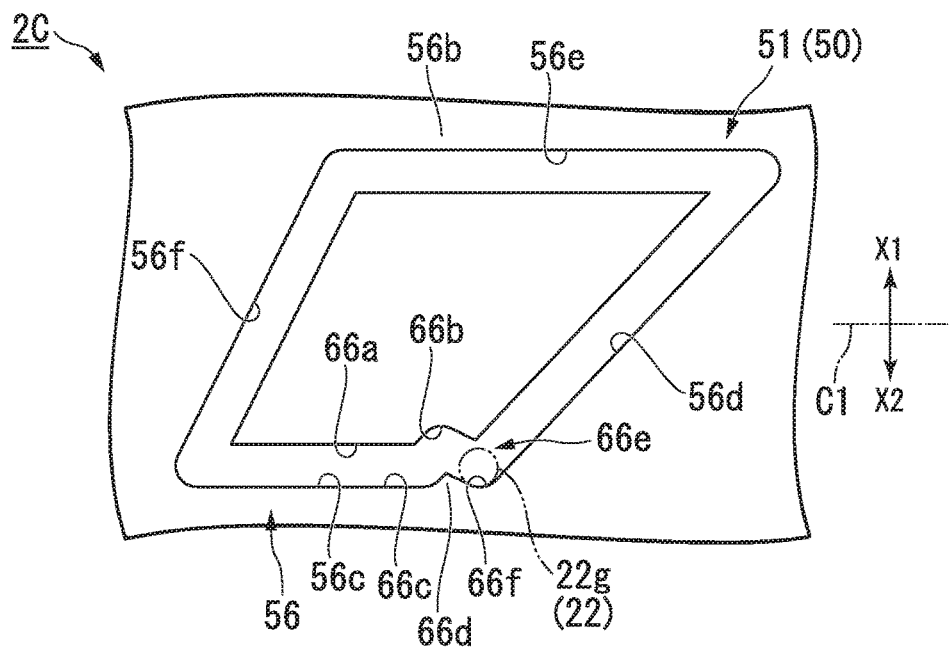
FIG. 16 is a deployed view of an outer peripheral surface of an operation part of a suture-needle holder in a modification example of the embodiment of the present invention.

As in a suture-needle holder 2C illustrated in FIG. 16, a recessed part 66b is formed at an end part on the second groove part 56d in a side surface 66a on the first side (first direction) X1 around the longitudinal axis C1 of the first groove part 56c, and a projecting part 66d may be formed on a side surface 66c on the second side (second direction) X2 around the longitudinal axis C1 of the first groove part 56c. A meandering part 66e in which the first groove part 56c meanders is formed by the recessed part 66b and the projecting part 66d.

Once the protruding part 22g is disposed at the second groove part 56d from the first groove part 56c, an elastic force to move the protruding part 22g to the second side (second direction) X2 around the longitudinal axis C1 is exerted by the coil spring 24 by the proximal end side of the coil spring 24 being twisted to the first side (first direction) X1 around the longitudinal axis C1.

For this reason, if the force with which the surgeon pulls back the slider 52 is loosened, the protruding part 22g is housed within a depression 66f formed adjacent to the proximal end side of the projecting part 66d in the side surface 66c of the first groove part 56c. It is preferable that a length by which the projecting part 66d protrudes from the side surface 66c of the first groove part 56c is equal to or greater than a certain value.

By forming the meandering part 66e at the end part of the first groove part 56c on the second groove part 56d side, the protruding part 22g is housed within the depression 66f, so that the protruding part 22g can be more reliably prevented from returning to the inside of the first groove part 56c from the inside of the second groove part 56d.

The protruding part 22g easily passes through the first groove part 56c to the proximal end side by not only the projecting part 66d but also the recessed part 66b being formed.

Figure 17:
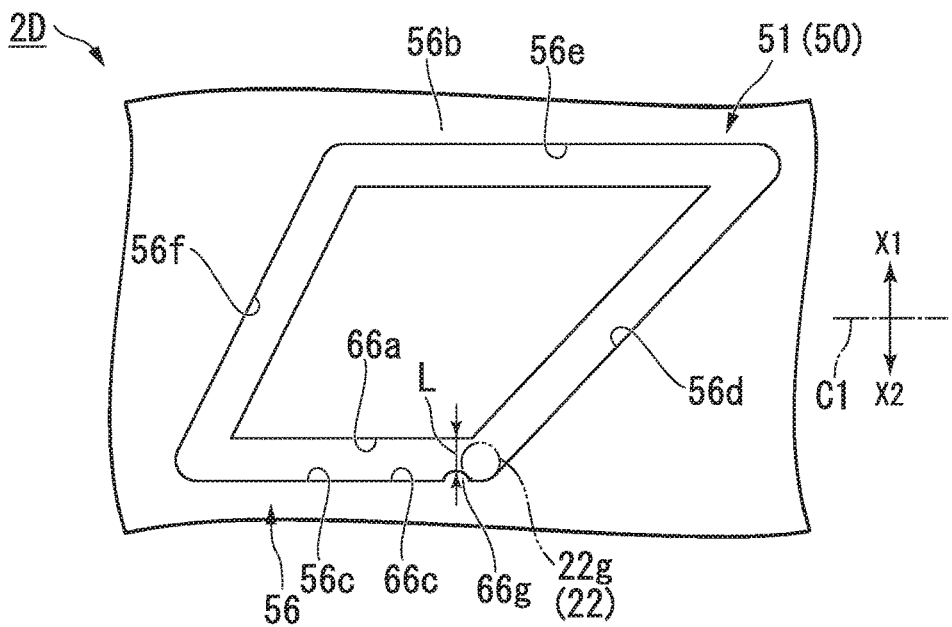
FIG. 17 is a deployed view of an outer peripheral surface of an operation part of a suture-needle holder in a modification example of the embodiment of the present invention.

As in a suture-needle holder 2D illustrated in FIG. 17, a second projecting part 66g may be formed at an end part on the second groove part 56d side in the side surface 66c of the first groove part 56c. The second projecting part 66g protrudes in a semicircular shape from the side surface 66c. A distance L between the side surface 66a and the second projecting part 66g is slightly smaller than the external diameter of the protruding part 22g.

When the protruding part 22g is moved to the proximal end side through between the side surface 66a and the second projecting part 66g, this passage is performed by the force with which that the surgeon pulls back the slider 52. Meanwhile, the spring constant of the coil spring 24 is made small, so that the elastic force of a coil spring 24 can prevent the protruding part 22g from moving to the distal end side between the side surface 66a and the second projecting part 66g.

The same effects as the suture-needle holder 2A of the modification example can be exhibited even if the second projecting part 66g in the end part on the second groove part 56d side in the side surface 66c of the first groove part 56c.

Although the one embodiment of the present invention has been described above in detail with reference to the drawings, specific configuration is not limited to this embodiment, and changes, combinations, deletions, or the like of the configuration are also included without departing from the scope of the present invention.

For example, in the embodiment, the groove parts 56e and 56f may not be formed in the outer peripheral surface 56b of the operation part body 51. This is because the operation of grasping the suture needle D1 to puncture of the tissue P1 with the suture needle D1 can be performed at a time if the groove parts 56c and 56d are formed in the outer peripheral surface 56b of the operation part body 51.

In this case, wall parts of regions RI and R2 between the engaging groove 22c and the key groove 22d in FIG. 7, and the larger-diameter part 22b may not be formed in the rotor 22. That is, with respect to the rotor 22, the sheath 21 just has to be locked to the first side (first direction) X1 and the second side (second direction) X2 around the longitudinal axis C1, and the distal end side, and may not be locked to the proximal end side.

Although the elastic member is the coil spring 24, the elastic member may be rubber or the like.

Additionally, the suture-needle holder 2 may not include the coil spring 24.

This is because a surgeon just has to push in and operate the slider 52.

Although the sheath 21 is fixed to the rotor 22 in a state where the sheath is inserted through the rotor 22, the rotor may be configured so as to be fixed to the sheath in a state where the rotor is inserted through the sheath.

The endoscope 3 includes the flexible insertion part 11. However, though the endoscope may include a rigid insertion part with greater bending rigidity than the flexible insertion part 11.

In the above embodiment, the operation part 50 is a slider-type handle. However, the operation part may be a so-called in-line type handle in which one end of the traction member is turnably attached to the operation part body and the proximal end part of the operation wire 40 is connected to the other end of this traction member. This is because the operation wire 40 can be moved in the direction aligned with the longitudinal axis C1 with respect to the sheath part 20 also by operating the traction member of the operation part.

While the preferred embodiment of the present invention has been described and illustrated above, it should be understood that the present invention is not limited to the embodiment and its modification example. Additions, omissions, substitutions, and other modifications of components can be made without departing from the concept of the present invention.

Additionally, the present invention is not to be considered as being limited by the foregoing description, and is limited only by the scope of the appended claims.

What is claimed is:

1. A suture-needle holder comprising:
a sheath part capable of being inserted into inside of a body;
a grasping portion fixed to at a distal end part of the sheath part and capable of grasping a suture needle with an opening and closing operation;
an operation wire connected to the grasping portion and operated to open and close the grasping portion by moving with respect to the sheath part along a longitudinal axis of the sheath part; and
an operation part body formed to extend along the longitudinal axis, and connected to the sheath part such that the sheath part is movable in a direction aligned with the longitudinal axis and rotatable around the longitudinal axis,
wherein a first groove part having a distal end and a proximal end and extending along the longitudinal axis, and a second groove part having one end connected to the proximal end of the first groove part and the other end at a position separated from the one end in a direction aligned with the longitudinal axis and in a circumferential direction of the longitudinal axis, and extending from the one end to the other end are formed in the operation part body,
wherein the sheath part is provided with a protruding part that protrudes in a radial direction of the sheath part,
wherein the protruding part has a first state where the protruding part moves in a state where the protruding part is engaged with the first groove part, and a second state where the protruding part moves in a state where the protruding part is engaged with the second groove part,
wherein in the first state, the operation wire is pulled with respect to the operation part body, and thereby the protruding part is moved from a distal end side of the first groove part to a proximal end side of the first groove part and the grasping portion is closed to grasp the suture needle, and
wherein in the second state, the operation wire in the first state is further pulled with respect to the operation part body, and thereby the protruding part is moved from the one end of the second groove part toward the other end of the second groove part, and the grasping portion and the sheath part are turned around the longitudinal axis with respect to the operation part body in a state where the grasping portion has grasped the suture needle.

2. The suture-needle holder according to claim 1, wherein the first groove part and the second groove part are formed in the outer peripheral surface of the operation part body, and the protruding part is provided at a proximal end part of the sheath part.

3. The suture-needle holder according to claim 2, wherein a third groove part having a distal end and a proximal end and extending along the longitudinal axis from the proximal end to the distal end, the proximal end being connected to the other end of the second groove part, and a fourth groove part extending around the longitudinal axis so as to connect the distal end of the third groove part and the distal end of the first groove part to each other are formed in the outer peripheral surface of the operation part body, wherein the protruding part has a third state where the protruding part moves in a state where the protruding part is engaged with the inside of the third groove part, and a fourth state where the protruding part moves in a state where the protruding part is engaged with the inside of the fourth groove part, wherein in the third state, the protruding part is moved from the proximal end side toward the distal end side within the third groove part, and the grasping portion is opened to release the suture needle, and wherein in the fourth state, if the protruding part is moved from the one end toward the other end within the fourth groove part, the grasping portion and the sheath part are turned in a direction opposite to a direction of turning of the grasping portion and the sheath part in the second state in a state where the grasping portion is open.

4. The suture-needle holder according to claim 2, further comprising an elastic member connected to the sheath part and the operation part body, respectively.

5. The suture-needle holder according to claim 2, wherein a proximal end part of the operation wire is provided with a traction member movably attached to the operation part body to move the operation wire in a direction aligned with the longitudinal axis with respect to the operation part body.

6. The suture-needle holder according to claim 5, further comprising:

a ratchet mechanism that allows movement of the traction member to the proximal end side with respect to the operation part body and restricts movement of the traction member to the distal end side when the protruding part is disposed within the first groove part, and allows the movements of the traction member to the proximal end side and the distal end side with respect to the operation part body when the protruding part is disposed within the second groove part.

7. The suture-needle holder according to claim 2, wherein a recessed part that is recessed toward the distal end side, is capable of housing at least a portion of the protruding part and is formed at an end part on the first groove part side in a side surface of the second groove part on the distal end side.

8. The suture-needle holder according to claim 7, wherein a projecting part that protrudes toward the distal end side is formed in a portion that faces the recessed part, in a side surface of the second groove part on the proximal end side.

9. The suture-needle holder according to claim 2, wherein a second projecting part is formed at an end part on the second groove part side in a side surface of the first groove part.

10. An endoscope system comprising:

the suture-needle holder according to claim 2; and an endoscope which has a flexible insertion part, and a channel through which the suture-needle holder is insertable provided in the insertion part.

* * * * *